United States Patent [19]
Dannenberg et al.

[11] Patent Number: 5,589,504
[45] Date of Patent: Dec. 31, 1996

[54] TREATMENT OF NEWBORN JAUNDICE

[75] Inventors: Andrew J. Dannenberg, New York; Jayanta R. Chowdhury, New Rochelle, both of N.Y.

[73] Assignees: Cornell Research Foundation, Inc., Ithaca; Albert Einstein College of Medicine of Yeshiva University, a Division of Yeshiva University, Bronx, both of N.Y.

[21] Appl. No.: 279,899

[22] Filed: Jul. 26, 1994

[51] Int. Cl.$^6$ .................... A61K 31/36; A61K 31/195; A61K 31/185; A61K 31/095
[52] U.S. Cl. .................... 514/456; 514/562; 514/578; 514/706; 514/731; 514/739; 514/764
[58] Field of Search .................... 514/706, 731, 514/562, 764, 739, 578, 456

[56] References Cited

U.S. PATENT DOCUMENTS

| | | | |
|---|---|---|---|
| 4,670,285 | 6/1987 | Clandinin et al. | 426/602 |
| 4,753,926 | 6/1988 | Lucas et al. | 514/2 |
| 5,234,702 | 8/1993 | Katz et al. | 426/72 |

OTHER PUBLICATIONS

Hankinson, O., Proc. Natl. Acad. Sci. USA 76, No. 1, 373–376, Jan. 1979.
Hankinson, O., Biochimie 73, 61–66 (1991).
Stern, L., et al, Am. J. Dis. Child, vol. 120, 26–31, Jul. 1970.
Sutherland, L., et al, Chemical Pharmacology, vol. 45, No. 2, 295–301, 1993.
Zhang, Y., et al, Proc. Natl. Acad. Sci. USA, vol. 89, 2399–2403, Mar. 1992.
Zhang, Y., et al, Proc. Natl. Acad. Sci. USA, vol. 91, 3147–3150, Apr. 1994.
Sutherland, L., et al, Biochemical Pharmacology, vol. 45, No. 2, 295–301, 1993.
Dannenberg A. J., et al, Programme and Abstracts, 7th International Workshop on Glucuronidation and the UDP–glucuronosyltransferases, p. 19, Sep. 1993.
Bosma, P. J., et al, Hepatology, vol. 18, No. 4, Pt 2, AASLD Abstracts, p. 127A, abstract 1283, 1993.
Cha, Y–N., et al, Cancer Research 42, 2609–2615, Jul. 1982.
Prestera, T., et al, Advan. Enzyme Regul., vol. 33, 281–296, 1993.
Prestera, T., et al, Proc. Natl. Acad. Sci USA, 90, 2965–2969 (Apr. 1993).
Talalay, P., "The Role of Enzyme Induction in Protection Against Carcinogenesis", In: Cancer Chemoprevention, L. Wassenberg et al, eds., CRC Press, Boca Raton, Fla., 469–478, 1992.
Dannenberg, A. J., et al, "Dietary Regulation of UDP–Glucuronosyltransferase, Glucuronidation Workshop", Scotland, Sep. 1993.
Prochaska, H. J., et al, Anal. Biochem. 169, 328–336 (1988).
Prochaska, H. J., et al, Proc. Natl. Acad. Sci. USA, 89, 2394–2398, Mar. 1992.
Yang, E. K., "Effect of Dietary Composition on Bilirubin–UDP–glucuronosyltransferase," presented Nov. 1993 in Chicago at meeting of American Association for Study of Liver Diseases.
Bergelson, S., et al, Oncogene 9: 565–571, 1994.
Bock, K. W., et al, Xenobiotica, 20, 1101–1111, 1990.
Owens, I. S., et al, Pharmacogenetics, 2, 93–108 (1992).
Posner, G. H., et al, J. Med. Chem. 37, 170–176 (1994).
Talalay, P., et al, Proc. Natl. Acad. Sci. USA, vol. 85, 8261–8265, Nov. 1988.
DeLong, M. J., et al, Proc. Natl. Acad. Sci. USA, vol. 83, 787–791, Feb. 1986.
DeLong, M. J., et al, Cancer Research 45, 546–551, Feb. 1985.
Rushmore, T. H., et al, The Journal of Biological Chemistry, vol. 266, No. 18, 11632–11639 (Jun. 1991).
Spencer, S. R., et al, Cancer Research 50, 7871–7875 (Dec. 1990).
Yang, E. K., et al, Hepatology, vol. 18, No. 4, Pt. 2, AASLD Abstracts, p. 127A, Abstract 282 (1993).
Yeung, C. Y., et al, Pediatrics, vol. 48, No. 3, 372–376 (Sep. 1971).

*Primary Examiner*—Theodore J. Criares

[57] ABSTRACT

Based on the discovery that the human bilirubin/phenol UDP-glucuronosyltransferase ugt1 gene complex contains an electrophile responsive element and the knowledge that the rat NADP(H):quinone reductase gene contains an electrophile responsive element, agents which at a concentration of less than 50 μM double the quinone reductase specific activity of Hepa 1c1c7 cells, e.g., BHT and sulforaphane, are used for the prophylaxis or treatment of newborn jaundice.

6 Claims, 1 Drawing Sheet

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
      ( A ) LENGTH: 10 base pairs
      ( B ) TYPE: nucleic acid
      ( C ) STRANDEDNESS: double
      ( D ) TOPOLOGY: linear ( i i ) MOLECULE TYPE: DNA (genomic)

( x i ) SEQUENCE DESCRIPTION: SEQ ID NO:1:

GTGACNNNGC          10

( 2 ) INFORMATION FOR SEQ ID NO:2:

( i ) SEQUENCE CHARACTERISTICS:
      ( A ) LENGTH: 11 base pairs
      ( B ) TYPE: nucleic acid
      ( C ) STRANDEDNESS: double
      ( D ) TOPOLOGY: linear ( i i ) MOLECULE TYPE: DNA (genomic)

( x i ) SEQUENCE DESCRIPTION: SEQ ID NO:2:

AGTGAGCAGG C          10

TREATMENT OF NEWBORN JAUNDICE

This invention was made at least in part under National Institutes of Health grant numbers DK 01992 and DK 39137. The Government has certain rights in the invention.

TECHNICAL FIELD

This invention is directed at prophylaxis or treatment of neonatal jaundice.

BACKGROUND OF THE INVENTION

Jaundice of the newborn results from the accumulation of bilirubin in blood. Elevations in the serum level of this end product of heme degradation occur because of delays in the normal postnatal development increase in bilirubin uridine-diphospho (UDP)-glucuronosyltransferase activity. This enzyme converts unconjugated bilirubin to bilirubin monoglucuronide and bilirubin diglucuronide which are excreted into bile and eliminated from the body. Treatment of jaundiced newborns is a major concern of pediatricians because bilirubin can enter neural tissues resulting in central nervous system toxicity. Thus, jaundice continues to be a common cause of prolonged hospitalization in newborns.

Phototherapy is the generally recommended form of treatment if bilirubin concentration reaches 14–15 mg/dl. An exchange transfusion is the generally recommended form of treatment if bilirubin concentration reaches levels of 20 mg/dl. These are complicated procedures and add to the expense of health care.

Phenobarbital has been administered to cause reduction of levels of serum bilirubin in newborns. Phenobarbital has been determined to function in this treatment by increasing the expression of the bilirubin/phenol UDP-glucuronosyltransferase ugt1 gene to cause increased levels of bilirubin UDP-glucuronosyltransferase activity. While this treatment increases the metabolism of bilirubin by upregulating the enzyme that is deficient in newborns, phenobarbital is not routinely used in the treatment of newborn jaundice because of its side effects, namely that it is habit-forming, causes drowsiness, can cause withdrawal problems and may be a cancer causer and/or promoter.

Recently, the Wall street Journal published an article about treating newborn jaundice by administering protoporphyrins, e.g., tin protoporphyrin. This treatment appears to be addressed in U.S. Pat. Nos. 4,831,024 and 5,081,115. The protoporphyrins function by inhibiting the breakdown of heme but do not cause an increase in bilirubin UDP-glucuronosyltransferase activity, i.e., upregulate the enzyme that is deficient in newborns.

SUMMARY OF THE INVENTION

It has been discovered herein that the human ugt1 gene that encodes bilirubin UDP-glucuronosyltransferase has an electrophile responsive element which is transcriptionally activated to cause induction of bilirubin UDP-glucuronosyltransferase. A functional electrophile responsive element is present in the rat NADP(H):quinone reductase gene. The invention herein involves the conception that, therefore, inducers of said quinone reductase gene, that act via the electrophile responsive element, when administered to newborns will induce the said human gene to increase the level and activity of bilirubin UDP-glucuronosyltransferase to correct the reduced level of this enzyme detected in neonatal jaundice and thereby increase the conjugation and clearance of bilirubin.

The invention herein is directed at a method of prophylaxis or treatment of newborn jaundice comprising administering to a subject in need of said prophylaxis or treatment a therapeutically effective amount of a non-toxic agent which is not habit-forming and which does not cause drowsiness and which at a concentration of less than 50 µM doubles the specific activity of quinone reductase in Hepa 1c1c7 cells. Many of these agents double the specific activity of quinone reductase in Hepa 1c1c7 cells at a concentration of less than 10 µM. Preferred agents are butylated hydroxytoluene and sulforaphane.

The human gene referred to is the bilirubin/phenol UDP-glucuronosyltransferase ugt1 gene. A schematic of this gene is depicted in FIG. 1. This gene is described in Owens, I. S., et al, Pharmacogenetics 2, 93–108 (1992). It is located at 2q37 on chromosome 2.

This human gene encodes at least two isoforms of bilirubin UDP-glucuronosyltransferase. The physiologically important isoform in normal human liver is known as bilirubin UDP-glucuronosyltransferase-1. See Bosma, P. J., et al, Hepatology, Vol. 18, No. 4, Pt. 2, page 127A, abstract 283, 1993.

We turn now to the term "electrophile responsive element." Various genes, e.g., the rat glutathione S-transferase Ya subunit gene and the rat NADP(H):quinone reductase gene have been known to contain an "antioxidant responsive element." See Rushmore, T. H., et al, The Journal of Biological Chemistry, Vol. 266, No. 18, 11632–11639, Jun. 25, 1991. This "antioxidant responsive element" is known to respond to metabolites of planar aromatic compounds, phenolic antioxidants and to peroxides. It has been recognized that the term "antioxidant responsive element" is a misnomer and the term "electrophile responsive element" has been suggested for use instead. See Prestera, T., et al, Advan. Enzyme Regul., Vol. 33, pp. 281–296, 1993 and Prestera, T., et al, Proc. Natl. Acad. Sci. USA, Vol. 90, pp. 2965–2969, April 1993. The terminology "electrophile responsive element" is used herein to refer to a nucleotide sequence in a gene that mediates the enhancement of gene expression by metabolites of planar aromatic compounds and phenolic antioxidants and by reactive oxygen species including peroxides.

The term "prophylaxis" is used herein to mean administration to a newborn at days 1 to 14 after birth having a serum bilirubin concentration of 5–10 mg/dl within the first 24 hours after birth and/or 10–12 mg/dl within the second 24 hours and/or during the third 24 hours after birth.

The term "treatment" is used herein to mean administration to a newborn (no more than 60 days old) having a serum bilirubin concentration of at least 13 mg/dl.

The term "therapeutically effective amount" is used herein to mean an amount that is effective in reducing serum bilirubin concentration to a level that does not cause neurological toxicity.

The specific activity being doubled is the basal specific activity of quinone reductase in the assay described below. The basal specific activity is the quinone reductase specific activity of Hepa 1c1c7 cells in the assay described below with vehicle being present but no inducer.

The quinone reductase referred to is the NADP(H):(quinone-acceptor) oxidoreductase (EC 1.6.99.2).

The Hepa 1c1c7 cells are available as a cell line from the tissue culture cell collection of the American Type Culture Collection, 12301 Parklawn Drive, Rockville, Md. 10852-1776 and are designated by the American Type Culture Collection by accession no. ATCC CRL 2026.

Concentration of compound that doubles the quinone reductase specific activity of Hepa 1c1c7 cells is sometimes referred to hereinafter as the CD.

DETAILED DESCRIPTION

Figure 1:
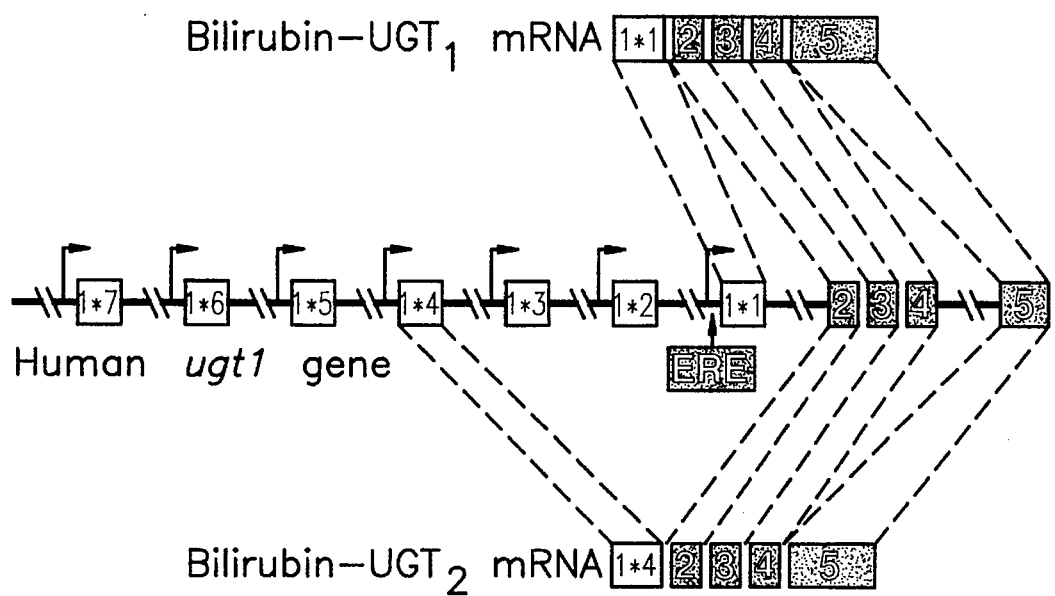
FIG. 1 schematically depicts the structure of the human bilirubin/phenol UDP-glucuronosyltransferase ugt1 gene.

We turn firstly to the agents for use herein.

As described above, these are non-toxic agents which are not habit-forming and do not cause drowsiness and which at a concentration of less than 50 μM double the specific activity of quinone reductase in Hepa 1c1c7 cells.

The determination of whether an agent meets the limitation of doubling the quinone reductase specific activity of Hepa 1c1c7 cells, at a concentration of less than 50 μM, is carried out by growing the cells in 96-well microtiter plates (10,000 cells per well) for 24 hours in medium containing 10% fetal calf serum, then exposing the cells to serial dilutions of agent for 48 hours and then measuring the quinone reductase specific activity on cell lysates. The determination is described in detail in Prochaska, H. J., et al, Anal. Biochem. 169, 328–336 (1988). The procedure as described in Prochaska et al can be modified by use of fetal calf serum which is heated for 90 minutes at 55° C. in the presence of activated charcoal and use of acetonitrile or dimethylformamide or water for dissolving agents to be assayed rather than DMSO (dimethyl sulfoxide) and adjustment of final organic solvent level to concentrations of 0.2% by volume or less, rather than to 0.1% by volume DMSO, e.g., 0.2% by volume DMSO or 0.1% by volume acetonitrile or as described in Posner, G. H., J. Med. Chem. 37, 170–176 (1994).

There are numerous articles directed to induction of enzymes that protect against chemical carcinogenesis (namely glutathione S-transferases, phenol isoform of UDP-glucuronosyltransferases and quinone reductase) which present data on the concentration of inducer that doubles the quinone reductase specific activity of Hepa 1c1c7 cells. These include, Spencer, S. R., et al, Cancer Research 50, 7871–7873, Dec. 15, 1990; Zhang, Y., et al, Proc. Natl. Acad. Sci. USA, Vol 89, pp. 2399–2403, March 1992; Prestera, T., et al, Proc. Natl. Acad. Sci USA, Vol. 90, pp. 2965–2969, April 1993; and Posner, G. H., et al, J. Med. Chem., 37, 170–176, 1994. The data of these articles is incorporated herein by reference.

The term "non-toxic" agent is used herein to exclude agents containing heavy metals or arsenic.

The characterization of the agents herein as not habit-forming and as not causing drowsiness excludes phenobarbital and distinguishes the invention from the use of phenobarbital for the treatment of newborn jaundice.

Compounds that are described in the literature as having the required CD and which are suitable as the non-toxic agents herein are found in the following groups: (1) Michael reaction acceptors; (2) diphenols and quinones and compounds which are metabolized to these in Hepa 1c1c7 cells; (3) isothiocyanates; (4) fumaric and maleic acid derivatives; (5) miscellaneous.

Michael reaction acceptors are characterized by olefinic or acetylenic bonds that are rendered electrophilic (positively charged) by conjugation with electron withdrawing substituents and are discussed in Talalay, P., et al, Proc. Natl. Acad. Sci. USA, Vol 85, pp 8261–8265, November 1988 and in Prestera, T., et al, Proc. Natl. Acad Sci. USA, Vol. 90, pp 2965–2969, April 1993. Michael reaction acceptors which are indicated in the literature to meet the CD limitation herein include 1-nitro-1-cyclohexene, 3-methylene-2-norbornanone, 2-methylene-4-butyrolactone, 5,6-dihydro-2H-pyran-2-one and 1-cyclohexen-2-one. See Prestera, T., et al, Proc. Natl. Acad. Sci. USA, Vol. 90, pp 2965–2969, April 1993.

Diphenols, quinones and compounds which are metabolized to these in Hepa 1c1c7 cells that are indicated in the literature to meet the CD limitation herein include the oxidizable diphenols hydroquinone, catechol and tert-butylhydroquinone and butylated hydroxytoluene, i.e., 2,6-bis(1,1-dimethyl-ethyl)-4-methylphenol, and butylated hydroxyanisole which is a mixture of 2-tert-butyl-4-methoxyphenol and 3-tert-butyl-4-methoxyphenol. See Prestera, T., et al, Proc. Natl. Acad. Sci. USA, Vol 90, pp. 2965–2969, April 1993 and De Long, M. J., et al, Proc. Natl. Acad. Sci., USA, Vol. 83, pp. 787–791, February 1986.

Isothiocyanates which are indicated in the literature to meet the CD limitation herein include benzyl isothiocyanate, sulforaphane and various analogs of sulforaphane. See Prestera, T., et al, Proc. Natl. Acad. Sci. USA, Vol. 90, pp. 2965–2969, April 1993; Zhang, Y., et al, Proc. Natl. Acad. Sci USA, Vol. 89, pp. 2899–2403, March 1992; and Posner, G. H., et al, J. Med. Chem. 37, 170–176 (1994).

Sulforaphane has the formula $CH_3$—$S(O)$—$(CH_2)_4$—$N$=$C$=$S$ and may be identified as (-)-1-isothiocyanato-(4R)-(methylsulfinyl) butane and has been isolated from and identified in SAGA broccoli (*Brassica olerocea italica*). (R,S)-Sulforaphane (CAS 4478-93-7) may be prepared as described in Schmid et al, Helv. Chim. Acta 31, 1497–1505 (1948). A variation on the method of Schmid et al is to use sodium thiomethoxide in place of gaseous thiomethanol.

The sulfoxide analogs of sulforaphane that are indicated in the literature to meet the CD limitation herein include iberin (CAS 505-44-2), i.e., $CH_3$—$S(O)$—$(CH_2)_3$—$N$=$C$=$S$, and alyssin (CAS 646-23-1), i.e., $CH_3$—$S(O)$—$(CH_2)_5$—$N$=$C$=$S$. See Zhang, Y., et al, Proc. Natl. Acad. Sci. USA, Vol. 89, pp. 2399–2403, March 1992. These can be prepared by the same general method as sulforaphane.

The sulfide analogs of sulforaphane that are indicated in the literature to meet the CD limitation herein are iberverin (CAS 505-79-3), i.e., $CH_3$—$S$—$(CH_2)_3$—$N$=$C$=$S$; erucin (CAS 4430-36-8), i.e., $CH_3$—$S$—$(CH_2)_4$—$N$=$C$=$S$; and berteroin (CAS 4430-42-6), i.e., $CH_3$—$S$—$(CH_2)_5$—$N$=$C$=$S$. See Zhang, Y., et al, Proc. Natl. Acad. Sci. USA, Vol. 89, pp 2399–2403, March 1993. Iberverin can be prepared by the method of Schmid, H., et al, Helv. Chim. Acta 31, 1497–1505 except using phthalimidopropyl bromide. Erucin and berteroin can be prepared as described in Kjaer, A., et al, Acta Chem. Scand. 9, 1311–1316 (1955).

The sulfone analogs of sulforaphane that are indicated in the literature to meet the CD limitation herein are cheirolin (CAS 505-34-0), i.e., $CH_3$—$SO_2$—$(CH_2)_3$—$N$=$C$=$S$; erysolin (CAS 504-84-7), i.e., $CH_3$—$SO_2$—$(CH_2)_4$—$N$=$C$=$S$; and $CH_3$—$SO_2$—$(CH_2)_5$—$N$=$C$=$S$. See Zhang, Y., et al, Proc. Natl. Acad. Sci. USA, Vol. 89, pp. 2399–2403, March 1993/ These can be prepared by the method of Schneider, W., et al, Liebigs Ann. Chem. 391-15 (1912).

Acyclic analogs of sulforaphane wherein the methylsulfinyl group of sulforaphane was replaced by other polar groups that are indicated in the literature to meet the CD limitation herein include those where the replacement group is $N{\equiv}C$, HOOC, MeOOC, MeSCO, MeCO, n-BuCO and $Me_2P({=}O)$. See Posner, G. H., et al, J. Med. Chem. 37, 170–176, 1994. The syntheses of the compounds where the replacement group is MeCO, i.e., 2-oxohexyl isothiocyanate, and where the replacement group is $Me_2P({=}O)$, i.e., (4-isothiocyanatobutyl)dimethylphosphine oxide are described in said Posner et al article.

Monocyclic analogs of sulforaphane that are indicated in the literature to meet the CD limitation herein include sulfonyl isothiocyanate, cis-(3-(methylsulfonyl)cyclohexyl)methyl isothiocyanate and trans-(3-(methylsulfonyl)cyclohexyl)methyl isothiocyanate. See Posner, G. H., et al, J. Med. Chem. 37, 170–176, 1994. The synthesis of these compounds is described in said Posner et al article.

Bicyclic analogs of sulforaphane that are indicated in the literature to meet the CD limitation herein are the following with a four carbon link between functionalities, namely, exo-2-methylsulfonyl-exo-5-isothiocyanatonorbornane, exo-2-acetyl-exo-5-isothiocyanatonorbornane, exo-2-cyano-exo-5-isothiocyanatonorbornane, exo-2-nitro-exo-5-isothiocyanatonorbornane, exo-2-methoxycarbonyl-exo-5-isothiocyanatonorbornane, and exo-2-(1'-hydroxyethyl)-exo-5-isothiocyanatonorbornane, and the following with a 3 carbon link between functionalities, namely, endo-2-methylsulfonyl-exo-6-isothiocyanatonorbornane, endo-2-acetyl-exo-6-isothiocyanatonorbornane, exo-2-methyl-exo-6-isothiocyanatonorbornane, exo-2 -acetyl-exo-6-isothiocyanatonorbornane, and exo-2-methoxycarbonyl-exo-6-isothiocyanatonorbornane. These are respectively compounds 21, 23, 24, 25, 26, 27, 20, 22, 29, 30 and 31 described in Posner, G. H., et al, J. Med. Chem., 37, 170–176, 1994 and the synthesis of these is described in said Posner et al article.

Aromatic analogs of sulforaphane that are indicated in the literature to meet the CD limitation herein are the benzylic isothiocyanates substituted in the ortho position by $CH_2SCH_3$, OMe, SMe, Me, and OEt. See Posner, G. H., et al, J. Med. Chem., 37, 170–176, 1994.

Another analog of sulforaphane that is indicated in the literature to meet the CD limitation herein is sulforaphene, i.e., $CH_3S(O)CH{=}CH(CH_2)_2N{=}C{=}S$. See Posner, G. H., et al, J. Med. Chem, 37, 170–176, 1994. It has been identified in radish seeds. Synthesis of it is described in Balenovic et al, Tetrahedron 22, 2139 (1966).

Fumaric and maleic acid derivatives that are indicated in the literature to meet the CD limitation herein are dimethyl fumarate (trans-$CH_3O_2CCH{=}CHCO_2CH_3$), dimethyl maleate (cis-$CH_3O_2CCH{=}CHCO_2CH_3$) and diethyl maleate (cis-$C_2H_5O_2CCH{=}CHCO_2C_2H_5$). See Spencer, S. R., et al, Cancer Research 50, 7871–7875, Dec. 15, 1990 and Talalay, P., Proc. Natl. Acad. Sci USA, Vol. 85, pp. 8261–8265 (November 1988).

Miscellaneous compounds that are indicated in the literature to meet the CD limitation herein are 1,2-dithiole-3-thione, β-naphthoflavone, methyl propiolate, i.e., $CH{\equiv}CCOOCH_3$ and crotonaldehyde. See Prestera, T., et al, Proc. Natl. Acad. Sci. USA, Vol. 90, 2965–2969, (April 1993) and Talalay, P., et al, Proc. Natl. Acad. Sci. USA, Vol. 85, pp 8261–8265 (November 1988).

We turn now to the therapeutically effective amount of agent as described above. As indicated above, the term "therapeutically effective amount" is used herein to mean an amount that is effective in reducing serum bilirubin concentration to a level that does not cause neurological toxicity. As indicated above, the administration herein causes the induction of enzymatic activity which causes conversion of bilirubin to excretable form.

The dosage constituting a therapeutically effective amount generally ranges from 1 to 10,000 mg/kg, preferably from 25 to 5,000 mg/kg, very preferably from 50 to 500 mg/kg. For butylated hydroxytoluene, a dosage of 250 mg/kg to 1000 mg/kg is considered to be preferred. For sulforaphane, a dosage of 50 to 250 mg/kg is considered to be preferred. These dosages are daily dosages. The dosage can be divided into, for example, 2 to 6 portions, administered at intervals, e.g., one-fourth of the daily dose every six hours or one-third of the daily dose every eight hours. Treatment is continued until physiological production of bilirubin UDP-glucuronosyltransferase activity becomes normal, typically for up to 10 days.

The preferred route of administration is oral. In such case, the agent herein is readily administered in a carrier that is normally consumed by the newborn, such as milk, or in one that is readily accepted, e.g., a sugar syrup. The agent may be administered in a nonionic emulsifying agent, e.g., Emulphor EL-620, Rhone-Poulenc, Cranbury, N.J., e.g., e.g., at a concentration of 0.02 to 0.1 gm/ml.

The administration is carried out less preferably via other routes, e.g., intramuscularly or intravenously. In such case the agent is administered together with a suitable carrier, e.g., saline or water for injection.

As indicated above, administration of agent within the scope of this invention may be carried out for prophylaxis (i.e., when bilirubin level in a newborn is higher than normal but not yet at a harmful level, e.g., a bilirubin level in the range of 5 to 10 mg/dl within the first 24 hours of life), or for treatment (i.e., when the bilirubin level in a newborn is at least 13 mg/dl and presents a risk of causing permanent damage).

The treatment herein can be used in combination with administration of protoporphyrins at established dosages to obtain the joint result of inhibition of breakdown of heme and increased conjugation and clearance of bilirubin.

The invention is illustrated in the following examples.

EXAMPLE I

Eighteen male Wistar rats weighing 200–250 g were divided into three groups. The first group of 6 rats received a control diet consisting of 21.0 grams of vitamin-free casein, 47.0 grams of sucrose, 22.5 grams Celufil (non-nutritive fiber), 5.0 grams corn oil, 4.0 grams USP XXI salt mixture (composition of salt mixture per 100 g of salt mixture: calcium carbonate, 38.14; cobalt chloride, 0.0023; copper sulfate, 0.0477; ferrous sulfate, 2.70; magnesium sulfate, 5.73; manganous sulfate, 0.401; potassium iodide, 0.079; potassium phosphate, monobasic, 38.90; sodium chloride, 13.93; and zinc sulfate, 0.0548), and 0.34 grams vitamin mix (g per 100 g diet: α-tocopherol, 0.022; L-ascorbic acid, 0.099; choline chloride, 0.165; D-calcium pantothenate, 0.0066; inositol, 0.011; menadione, 0.00495; niacin, 0.0099; p-aminobenzoic acid, 0.011; pyridoxine HCl, 0.0022; riboflavin, 0.0022; thiamine HCl, 0.0022; retinyl acetate, 0.00396; calciferon, 0.00044; biotin, 0.000044; folic acid, 0.000198; vitamin B-12, 0.002974), per 100 grams of diet. The second group of 6 rats received the control diet supplemented with 2(3)-tert-butyl-4-hydroxyanisole (BHA, 0.75%, w/w). The third group received the control diet supplemented with 2,6-di-tert-butyl-4-methylphenol (BHT, 0.5%, w/w). The diets were administered for 2 weeks as described in Chau, Y-N., et al, Cancer Res. 42, pp. 2609–2615 (1982).

At the end of the two week treatment, the rats were sacrificed by cervical dislocation and microsomes were prepared from the rat livers as described in Vessey, D. A., et al, J. Biol. Chem., 246, pp. 4649–4656 (1971). Protein concentration was determined by the method of Lowry, O. H., et al, J. Biol. Chem. 193: 265–275 (1951).

UDP-glucuronosyltransferase activities were assayed with bilirubin as substrate using a modification of the method of Burcheil, B., Methods in Enzymol. 77, pp. 188–192 (1981) as follows: Assays were performed in 0.3 ml of 0.1M triethanolamine-HCl buffer (pH 8.0) with $MgCl_2$ (1.6 mg/ml) with a final volume of 0.6 ml. A reaction mixture contained 200 µg microsomal protein activated with CHAPS {3-[(3-cholamidopropyl)dimethylamino]-1-propanesulfonate, 0.5%, w/w}, 5 mM UDP-glucuronic acid and 0.5 mM bilirubin. Incubation was performed at 37° C. for 20 min. Then 1 ml of 0.1 M glycine-HCl (pH 2.8) was immediately added to the mixtures on ice. Then 0.5 ml of ethyl anthranilate-diazo reagent prepared as described in Burcheil, B., Methods in Enzymol. 77, pp. 188–192, 1981, was added, and coupling was allowed to proceed at 25° C. for 30 min. The reaction was terminated by adding freshly made 10% ascorbic acid solution and the azopigment was extracted with 1 ml of 2-pentanone/butyl acetate (17:3, v/v). Absorbance of the organic phases was measured at 530 nm.

Bilirubin UDP-glucuronosyltransferase activity was 1.15±0.15 nmol/min/mg for the BHT-treated group, 0.65±0.08 nmol/min/mg for the BHA-treated group and 0.39±0.07 nmol/min/mg for the control group. This amounts to a 295% increase for BHT and a 167% increase for BHA.

Immunoblot analysis was carried out as follows: Sodium dodecyl sulfate-polyacrylamide gel electrophoresis (SDS-PAGE) was carried out under reducing conditions on 10% polyacrylamide gels as described in Laemmli, U. K., Nature (London), 227, pp. 680–685 (1970). Proteins were transferred from slab gels onto nitrocellulose membranes by the method of Towbin, H., et al, Proc. Natl. Acad. Sci. USA, 76, pp. 4350–4354 (1979). The transferred proteins were probed with either a polyclonal antiserum to UDP-glucuronosyltransferase or a peptide directed antibody specific for rat bilirubin-UDP-glucuronosyltransferase. Immunoreactive bands were visualized using a secondary antibody conjugated with alkaline phosphatase as described in Yang, E. K., et al, Biochim. Biophys. Acta. 1168, pp. 52–58 (1993). The analysis showed changes in amount of bilirubin UDP-glucuronosyltransferase corresponding to the differences in bilirubin UDP-glucuronosyltransferase activity.

Northern blot analysis was carried out as follows: Total cellular RNA from rat liver tissue was isolated from rat liver by the method described in Chomczynski, P., et al, Anal. Biochem., 162, pp. 156–159 (1987). Fifteen micrograms of total RNA was electrophoretically separated on 1% agarose gel containing 6% formaldehyde prior to transfer to Nytran membranes (Schleicher and Schuell, Keene, N.H.). The blot was prehybridized in 25% formamide, 6×SSC, 25 mM sodium phosphate, pH 7.4, 1% sodium dodecyl sulfate, 5×Denhardt's solution, and 100 µg/ml denatured salmon sperm DNA at 42° C. for 3 hours. After prehybridization, the blot was incubated in prehybridization solution containing [gamma-$^{32}$P]ATP-radiolabeled oligonucleotide probes coding for rat bilirubin UDP-glucuronosyltransferase or the common 3'-domain of the rat bilirubin/phenol UDP-glucuronosyltransferase. The blot was washed 1 hr. in 6×SSC containing 0.5% sodium dodecyl sulfate at 42° C., and subjected to autoradiography. For determination of the relative amounts of RNA in the various lanes, the blot was stripped of radioactivity and rehybridized with a rat alpha-tubulin probe. A computer densitometer (Molecular Dynamics, Sunnyvale, Calif.) was used to determine the density of the bands on the Northern blots. Hepatic concentrations of mRNAs for bilirubin UDP-glucuronosyltransferase isoform paralleled the concentration of enzyme protein and level of enzyme activity. This indicates that the increased bilirubin glucuronidation results from increased synthesis of the bilirubin UDP-glucuronosyltransferase enzyme.

While the experiment was carried out on rats, the rat UDP-glucuronosyltransferase gene, like the human ugt1 gene, contains an electrophile responsive element. See Bergelson, S., et al, Oncogene 9, pp. 565–571 (1994). Thus, the results obtained are similar to those that would be obtained on humans.

EXAMPLE II

Hepa 1c1c7 cells were plated at $2×10^6$ cells/plate in 15-cm plastic plates with 25 ml medium consisting of alpha-minimal essential medium supplemented with 10% charcoal and heat-treated fetal calf serum. Forty-eight hours later, the cells were exposed to fresh medium with 2 µM sulforaphane/0.02% acetonitrile or only acetonitrile for 24 hours. Cells were then collected and transferred to tubes containing DPBS buffer. The final cell density is $8–10×10^6$ cells/plate. The tubes were centrifuged at 2000 rpm×5 minutes to remove supernatant, leaving 0.25 ml DPBS in a tube with the cells. The tubes were immediately frozen in liquid nitrogen.

UDP-glucuronosyltransferase activity was measured in one tube of sulforaphane treated cells and one tube of control cells using 3-OH-benzo(a)pyrene as a substrate as follows: A cellular homogenate was prepared. Protein concentration was determined as described in Lowry, O. H., et al, J. Biol. Chem. 193, 265–275 (1951). The activity of UDP-glucuronosyltransferase was determined using 3-hydroxybenzo(a)pyrene as a substrate according to the method of Singh, J., et al, Anal. Biochem. 98, pp. 394–401 (1979). Each assay contained in a total volume of 1 mL, 100 mM Tris-HCl (pH 7.6), 5 mM $MgCl_2$, 0.0125% Triton X-100, 3 mM UDP-glucuronic acid, 50 µM 3-hydroxybenzo(a)pyrene and 50 µg of protein. The activity of UDP-glucuronosyltransferase was about 75% greater in sulforaphane treated cells (0.82 nmol/min/mg protein) than in control cells (0.47 nmol/min/mg). 3-Hydroxybenzo(a)pyrene was used as a substrate rather than bilirubin because the isoforms of UDP-glucuronosyltransferase which conjugate 3-hydroxybenzo(a)pyrene and bilirubin are coded for by the bilirubin/phenol UDP-glucuronosyltransferase ugt1 gene and the assay for 3-hydroxybenzo(a)pyrene is more sensitive than the assay for bilirubin and hence less protein is required. This is an important consideration given the relatively small amount of protein that is available from cells compared to animal tissues. The results based on 3-hydroxybenzo(a)pyrene as the substrate are considered to be similar to those that would be obtained based on bilirubin as the substrate.

Immunoblot analysis was carried out on one tube of sulforaphane treated cells and on one tube of control cells as follows: sodium dodecyl sulfate-polyacrylamide gel electrophoresis (SDS-PAGE) was carried out under reducing conditions on 10% polyacrylamide gels as described in Laemmli, U. K., Nature (London), 227, pp. 680–685 (1970). Proteins were transferred from slab gels onto nitrocellulose membranes by the method of Towbin, H., et al, Proc. Natl. Acad. Sci. USA, 76, pp. 4350–4354 (1979). The transferred proteins were probed with a polyclonal antiserum to UDP-glucuronosyltransferase. Immunoreactive bands were visualized using a secondary antibody conjugated with alkaline phosphatase as described in Yang, E. K., et al, Biochim. Biophys. Acta. 1168, pp. 52–58 (1993). This analysis showed that treatment with sulforaphane increased the amounts of UDP-glucuronosyltransferase in hepatocytes, consistent with its effect on enzyme activity.

EXAMPLE III

Other compounds were tested for UDP-glucuronosyltransferase activity by the method described in Example II except that the vials of cells and agent or control were prepared with the following differences. Concentration of agent tested is given below. Dimethylsulfoxide was utilized as the carrier at a final concentration of 0.02%. Harvesting was carried out by pooling the cells from three plates (approximately $13 \times 10^6$ cells per plate) for each inducer into one vial, rather than one vial per plate. Also, following centrifugation, the volume of DPBS plus cells was adjusted to one milliliter in each vial, leaving the pellet intact. Next, the pellet was resuspended via a one milliliter syringe equipped with a 22 gauge needle. Approximately 800 microliters of resuspended cells ($31-32 \times 10^6$ cells) were transferred to a two milliliter vial and immediately frozen in liquid nitrogen.

For 1 μM concentration β-naphthoflavone, the activity of UDP-glucuronosyltransferase was about 260% greater (1.694 nmol/min/mg protein) than in control cells (0.47 nmol/min/mg).

For 10 μM concentration benzyl isothiocyanate, the activity of UDP-glucuronosyltransferase was about 78% greater (0.837 nmol/min/mg protein) than in control cells (0.47 nmol/min/mg).

For 25 μM tert-butylhydroquinone, the activity of UDP-glucuronosyltransferase was about 87% greater (0.883 nmol/min/mg protein) than in control cells (0.47 nmol/min/mg).

For 50 μM dimethyl fumarate, the activity of UDP-glucuronosyltransferase was about 38% greater (0.649 nmol/min/mg protein) than in control cells (0.47 nmol/min/mg).

For 20 μM 1,2-dithiole-3-thione, the activity of UDP-glucuronosyltransferase was about 130% greater (1.084 nmol/min/mg protein) than in control cells (0.47 nmol/min/mg).

For 5 μM 1-nitro-1-cyclohexene, the activity of UDP-glucuronosyltransferase was about 87% greater (0.880 nmol/min/mg protein) than in control cells (0.47 nmol/min/mg).

An 80 Kb segment of the human genome spanning a large segment of the human bilirubin/phenol UDP-glucuronosyltransferase ugt1 gene was cloned in 5 cosmids. The region upstream to the unique exon of bilirubin UDP-glucuronosyltransferase-1 was sequenced.

The sequence was examined for an electrophile responsive element (antioxidant responsive element) based on homology to previously described elements exhibiting this function. The sequence puGTGACNNNGC where pu represents the generic purine residue and N is any nucleotide was previously identified as an antioxidant responsive element in Rushmore, T. H., et al, The Journal of Biological Chemistry, Vol. 266, No. 18, pp. 11632–11639 (Jun. 25, 1991). This sequence subsequent to pu is identified in the sequence listing herein as SEQ ID NO:1. A very similar sequence was found in base pairs 470–480 upstream to the translation initiation codon of the first exon (exon 1*1) of bilirubin UDP-glucuronosyltransferase-1 in the human ugt1 gene, namely the sequence AGTGAGCAGGC which is identified in the sequence listing herein as SEQ ID NO:2.

A fragment having the sequence of SEQ ID NO:2 was removed from the gene using restriction enzymes and is referred to hereinafter as the ERE (electrophilic responsive element) promoter.

Figure 2:
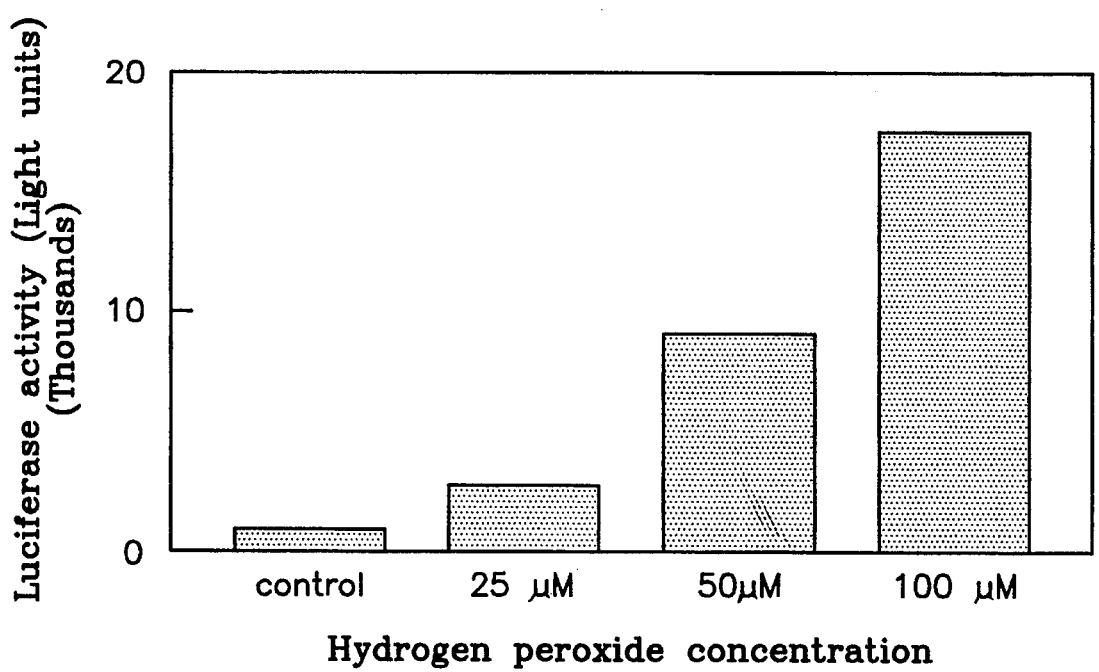
FIG. 2 depicts the effect of hydrogen peroxide on hB-UGT-1 transfected HUH-7 cells and shows results of Example IV.

The plasmid DNA constructs CpRSVluc (control) and pRSVluc (test plasmid containing the ERE promoter) were transfected for transient expression into the human hepatoma cell line HUH-7. The cells were plated at $2.5 \times 10^5$ cells per 35 mm tissue culture dish 24 hours before transfection. Transfection was carried out in serum-free medium by exposing the cells to plasmid DNA contruct-lipid complexes (ratio of plasmid DNA construct to lipofectin of 1:2, w/w) for 5 hours at 37° C. After transfection, the cells were exposed to different concentrations of $H_2O_2$ (25 μM, 50 μM, and 100 μM). At 100 μM $H_2O_2$, the reporter transgene luciferase activity increased approximately 10 fold when compared to the control. Stepwise increases in induction were detected at lower concentrations with the maximum increase being detected at 100 μM $H_2O_2$. The results are depicted in FIG. 2.

This shows that the sequence of SEQ ID NO:2 of the human gene does function as an electrophile responsive element. Since hydrogen peroxide also induces NAD-P(H):quinone reductase via an electrophile responsive element, other inducers of the rat NADP(H):quinone reductase gene will also induce the human bilirubin/phenol UDP-glucuronosyltransferase ugt1 gene.

REFERENCE EXAMPLE 1

Administration of phenobarbital is considered to cause reduction of levels in serum bilirubin in treatment of newborns for neonatal jaundice by inducing the bilirubin/phenol UDP-glucuronosyltransferase ugt1 gene to cause increased levels of bilirubin UDP-glucuronosyltransferase activity. See Stern, L., et al, Am. J. Dis. Child, Vol. 120, 26–31 (July 1970); and Yeung, C. Y., et al, Pediatrics, Vol. 48, No. 3, 372–376 (September 1971).

However, different mechanisms are involved in the induction by phenobarbital from the one involved in the present invention, as shown by the different induction pattern caused by phenobarbital from that caused by the agents herein.

In Example I herein, BHT and BHA were shown to cause increase in activity of UDP-glucuronosyltransferase for bilirubin of 295% and 167% respectively. In similar testing, BHT and BHA have been shown to cause an increase in the activity of UDP-glucuronosyltransferase for p-nitrophenol of 236% and 218%, respectively, and for androsterone of 269% and 152%, respectively.

On the other hand, phenobarbital has a minor effect on the conjugation of p-nitrophenol and does not induce the androsterone isoform of UDP-glucuronosyltransferase.

However, the fact that phenobarbital reduces the level of serum bilirubin by causing an increase in the activity of bilirubin UDP-glucuronosyltransferase evidences, in view of the discoveries herein, that administration of the agents herein also reduces serum bilirubin level.

EXAMPLE V

Two groups of 10, 24-hour old newborns, matched by gestational age, gender and birthweight and having the average serum bilirubin level of 6, are utilized in this experiment.

One group is administered BHT in a syrup by mouth at a dosage of 600 mg/kg daily (200 mg/kg every 8 hours) for 5 days.

The second group is administered only the syrup.

At the end of the 5-day period, the treated group has a significantly reduced average serum bilirubin level while the control group has an average increased serum bilirubin level.

Similar results of serum bilirubin level reduction are obtained when the BHT is administered intramuscularly or intravenously instead of by mouth.

EXAMPLE VI

Two groups of 10, 24-hour old newborns, matched by gestational age, gender and birthweight and having an average bilirubin level of 6, are utilized in this experiment.

One group is administered sulforaphane in a syrup by mouth at a dosage of 150 mg/kg daily (50 mg/kg every 8 hours) for 5 days.

The second group is administered only the syrup.

At the end of the 5-day period, the treated group has an average serum bilirubin level of less than 2 whereas the control group has an average increased serum bilirubin level.

Similar results of serum bilirubin level reduction are obtained when the sulforaphane is administered intramuscularly or intravenously instead of by mouth.

Variations in the invention will be obvious to those skilled in the art. Thus, the invention is defined by the claims.

What is claimed is:

1. A method of prophylaxis or treatment of newborn jaundice comprising administering to a subject in need of said prophylaxis or treatment a therapeutically effective amount of a compound which is not habit-forming and which does not cause drowsiness and which does not contain heavy metals or arsenic and which at a concentration of less than 50 μM doubles the quinone reductase specific activity of Hepa 1clc7 cells, said compound being selected from the group consisting of Michael reaction acceptors; diphenols, quinones and compounds which are metabolized to these in Hepa 1clc7 cells; isothiocyanates; fumarates; maleates; 1,2-dithiole-3-thione; beta-naphthoflavone; methyl propiolate; and crotonaldehyde.

2. A method of prophylaxis or treatment of newborn jaundice comprising administering to a subject in need of said prophylaxis or treatment, a therapeutically effective amount of a compound which at a concentration of less than 50 μM doubles the quinone reductase specific activity of Hepa 1clc7 cells and which does not contain heavy metals or arsenic and is not phenobarbital, said compound being selected from the group consisting of Michael reaction acceptors; diphenols, quinones and compounds which are metabolized to these in Hepa 1clc7 cells; isothiocyanates; fumarates; maleates; 1,2-dithiole-3-thione; beta-napthoflavone; methyl propiolate; and crotonaldehyde.

3. The method of claim 1 wherein the compound is selected from the group consisting of isothiocyanates.

4. The method of claim 1 wherein the compound is selected from the group consisting of diphenols, quinones and compounds which are metabolized to these in Hepa 1c1c7 cells.

5. The method of claim 4 wherein the compound is butylated hydroxytoluene.

6. The method of claim 3 wherein the compound is $CH_3-S(O)-(CH_2)_4-N=C=S$.

* * * * *